United States Patent
Konishi

(10) Patent No.: US 8,792,612 B2
(45) Date of Patent: Jul. 29, 2014

(54) RADIATION IMAGING SYSTEM, CONTROL METHOD FOR THE SAME, AND PROGRAM

(75) Inventor: Shimpei Konishi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 106 days.

(21) Appl. No.: 12/844,737

(22) Filed: Jul. 27, 2010

(65) Prior Publication Data

US 2011/0026677 A1 Feb. 3, 2011

(30) Foreign Application Priority Data

Jul. 31, 2009 (JP) ................................ 2009-179628

(51) Int. Cl.
- G01N 23/083 (2006.01)
- H05G 1/64 (2006.01)
- G06K 9/20 (2006.01)

(52) U.S. Cl.
USPC ........ 378/62; 378/98.8; 250/370.09; 382/132

(58) Field of Classification Search
USPC ........ 378/98.7, 108, 109, 110, 111, 112, 207, 378/98.8, 62; 382/132, 207; 250/370.09
See application file for complete search history.

(56) References Cited

U.S. PATENT DOCUMENTS

| | | | | |
|---|---|---|---|---|
| 6,084,939 | A * | 7/2000 | Tamura | 378/98.2 |
| 6,244,507 | B1 * | 6/2001 | Garland et al. | 235/383 |
| 6,362,482 | B1 * | 3/2002 | Stettner et al. | 250/370.08 |
| 6,470,071 | B1 * | 10/2002 | Baertsch et al. | 378/62 |
| 6,614,877 | B2 * | 9/2003 | Anderton | 378/98.7 |
| 6,768,784 | B1 * | 7/2004 | Green et al. | 378/62 |
| 6,806,487 | B2 * | 10/2004 | Tamakoshi et al. | 250/586 |
| 6,850,634 | B1 * | 2/2005 | Shinbata | 382/132 |
| 6,855,936 | B2 * | 2/2005 | Yamamoto | 250/370.09 |
| 6,901,158 | B2 * | 5/2005 | Shinbata | 382/132 |
| 6,904,181 | B1 * | 6/2005 | Shinbata et al. | 382/282 |
| 7,013,035 | B2 * | 3/2006 | Shinbata | 382/132 |
| 7,088,851 | B2 * | 8/2006 | Shinbata | 382/132 |
| 7,116,752 | B2 * | 10/2006 | Takahashi et al. | 378/62 |
| 7,120,229 | B2 * | 10/2006 | Takasawa | 378/98.2 |
| 7,123,761 | B2 * | 10/2006 | Kawano | 382/132 |
| 7,359,541 | B2 * | 4/2008 | Kawano | 382/132 |
| 7,476,027 | B2 * | 1/2009 | Takenaka et al. | 378/207 |
| 7,476,834 | B2 * | 1/2009 | Umeki et al. | 250/208.1 |
| 7,522,697 | B2 * | 4/2009 | Satta et al. | 378/15 |

(Continued)

FOREIGN PATENT DOCUMENTS

| JP | 5192318 A | 8/1993 |
|---|---|---|
| JP | 8147456 A | 6/1996 |

(Continued)

Primary Examiner — Allen C. Ho
(74) Attorney, Agent, or Firm — Canon USA Inc. IP Division

(57) ABSTRACT

A radiation imaging system includes a radiation sensor unit and a main control unit. The radiation sensor unit includes, a radiation sensor that detects a radiation image based on radiation that passes through an object, a sensor characteristics correction unit that performs sensor characteristics correction on the radiation image based on image reception characteristics of the radiation sensor, an image analysis unit that analyzes the radiation image in which the sensor characteristics correction has been performed and calculates an analysis parameter, and a transmission unit that transmits the analysis parameter as a gradation conversion parameter and the radiation image which has been subjected to the sensor characteristics correction to the main control unit. The main control unit includes a gradation conversion processing unit that performs gradation conversion processing on the radiation image which has been subjected to the sensor characteristics correction using the gradation conversion parameter.

12 Claims, 11 Drawing Sheets

(56) References Cited

U.S. PATENT DOCUMENTS

| | | | |
|---|---|---|---|
| 7,545,914 B2 * | 6/2009 | Kito et al. | 378/98.8 |
| 7,680,315 B2 * | 3/2010 | Roehrig et al. | 382/132 |
| 7,724,934 B2 * | 5/2010 | Shinbata | 382/132 |
| 7,767,981 B2 * | 8/2010 | Kuwabara et al. | 250/484.4 |
| 8,193,509 B2 * | 6/2012 | Niekawa et al. | 250/370.09 |
| 8,194,824 B2 * | 6/2012 | Takahashi | 378/108 |

FOREIGN PATENT DOCUMENTS

| | | |
|---|---|---|
| JP | 10-285466 A | 10/1998 |
| JP | 2001-325594 A | 11/2001 |
| JP | 2002158876 A | 5/2002 |
| JP | 2005328940 A | 12/2005 |
| JP | 2006-043293 A | 2/2006 |
| JP | 2008229102 A | 10/2008 |
| JP | 2009156936 A | 7/2009 |

* cited by examiner

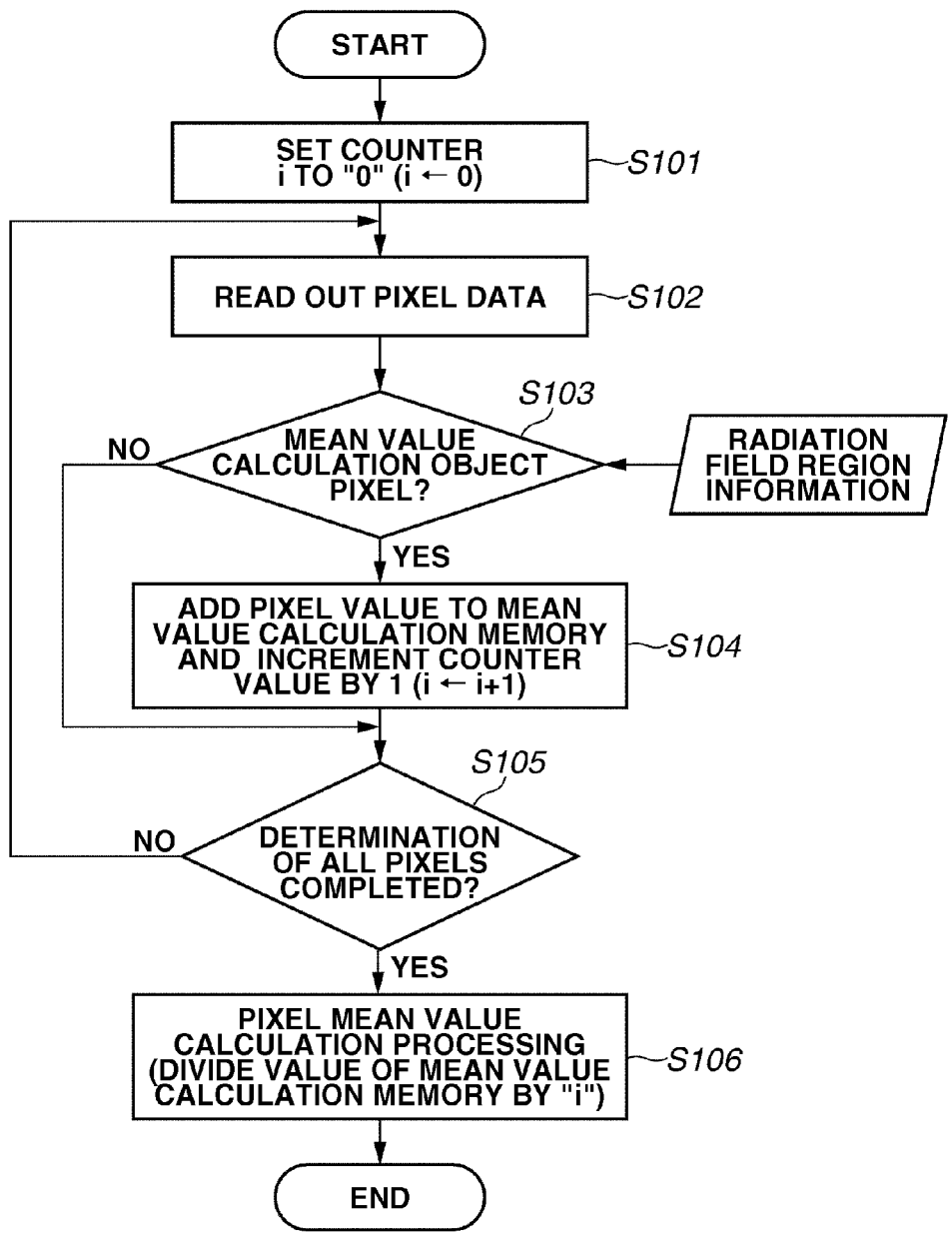

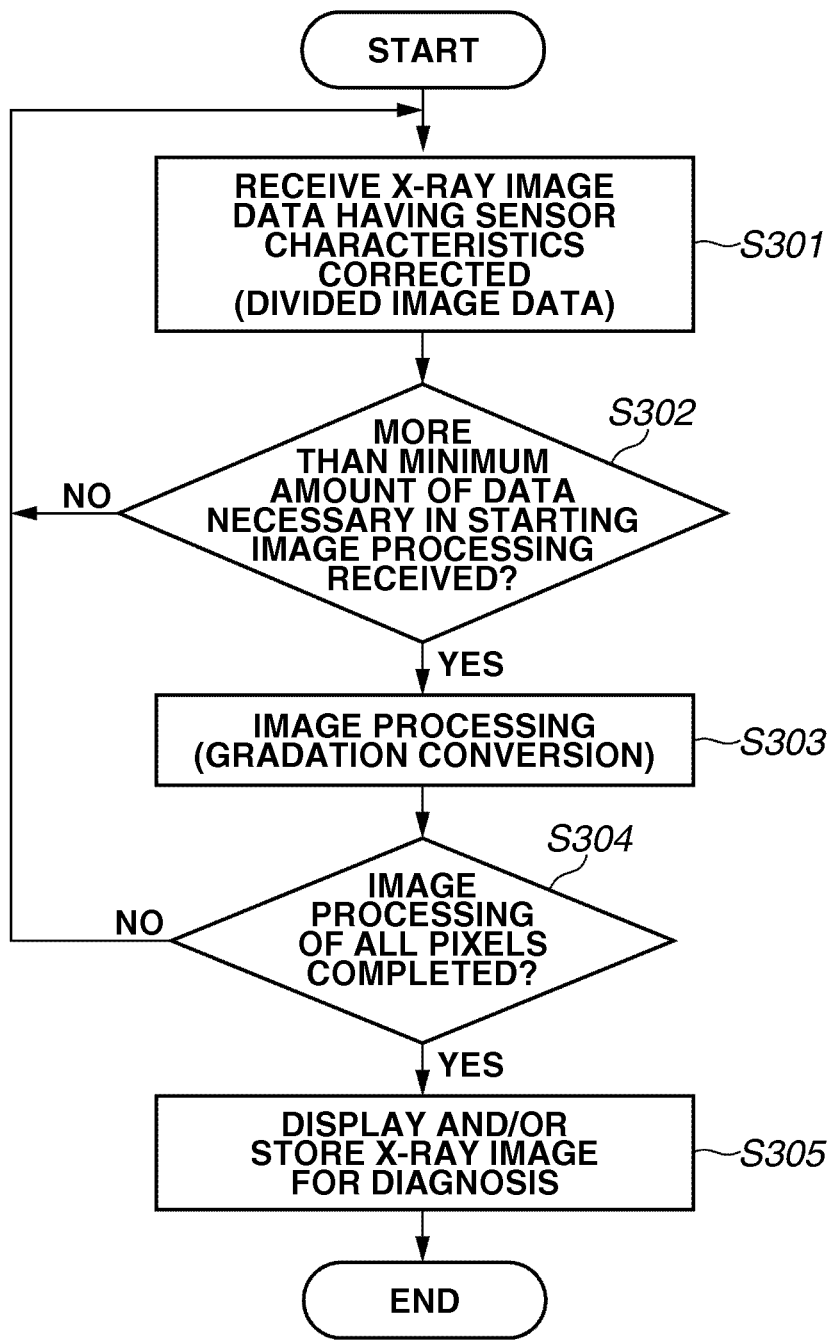

RADIATION IMAGING SYSTEM, CONTROL METHOD FOR THE SAME, AND PROGRAM

BACKGROUND OF THE INVENTION

1. Field of the Invention

The present invention relates to a radiation imaging system capable of capturing a radiation image of an object using a radiation ray that passes through the object, a control method of the system, and a program used for causing a computer to execute the control method.

2. Description of the Related Art

An X-ray imaging apparatus is used for capturing an image using X-ray which is one type of radiation rays. In recent years, a digital X-ray imaging apparatus using a photoelectric conversion element has been used in acquiring intensity distribution of an X-ray beam that passed through an object. The digital X-ray imaging apparatus is considered advantageous over a conventional film-type imaging apparatus in that it can produce images with high sensitivity and better image quality. Further, since the images captured by the digital X-ray imaging apparatus are stored in digital data, various types of image processing can be performed after the imaging, and the captured images can be processed into images that can be easily diagnosed. Further, the digital X-ray imaging apparatus is advantageous to management of the captured images and transfer of the image data via a network.

Generally, when X-ray imaging is performed, a space where the imaging is actually performed by irradiating X-ray is different from a space where the X-ray imaging apparatus is controlled and an obtained image is displayed for diagnosis. Further, a room where the imaging is performed and a room where the control is performed can be different depending on an imaging style. This is because there is a need for separately using an "X-ray sensor unit" which is used for actually taking the X-ray image, and a "main control unit" which controls the apparatus and performs image processing.

In an X-ray imaging system including such an X-ray sensor unit and a main control unit, the X-ray sensor unit includes an X-ray sensor portion for acquiring an X-ray image of an object and also a communication interface (I/F) for transmitting the acquired image data to a distant main control unit. The X-ray sensor unit performs an imaging operation according to an instruction given from the main control unit. On the other hand, the main control unit includes an image processing unit which converts the image data transmitted from the X-ray sensor unit into image data appropriate for a diagnosis, a control unit which controls the X-ray imaging system, and a user I/F.

The X-ray sensor portion in the X-ray sensor unit includes a two-dimensional array of conversion elements and switching elements such as a thin film transistor (TFT). In obtaining an X-ray image of an object, the object is positioned between an X-ray source and the X-ray sensor unit. Then, an amount of X-ray that passed through the object is converted into an electric signal by each conversion element. In this way, the X-ray image is obtained. Further, the electric signal (X-ray image signal) output from each conversion element is individually read out and digitized according to analog-to-digital (A/D) conversion.

In recent years, an X-ray sensor portion which can capture moving images as well as still images has been developed. Such units are discussed, for example, in Japanese Patent Application Laid-Open No. 10-285466 and Japanese Patent Application Laid-Open No. 2006-43293. From the viewpoint of work efficiency and space savings, there is a growing demand for an X-ray imaging apparatus which can capture moving images and still images.

The X-ray image obtained by the X-ray sensor portion includes image reception characteristics (sensor characteristics), such as variation in a stationary noise and sensitivity characteristics. Since the sensor characteristics are unique to the X-ray sensor portion, they need to be corrected. For example, the X-ray sensor unit corrects the sensor characteristics and outputs an X-ray image having the sensor characteristics corrected to the main control unit of a subsequent stage. The main control unit processes the X-ray image transmitted from the X-ray sensor unit so that the X-ray image can be diagnosed more easily. The processing performed by the main control unit includes, for example, sharpening the image, reducing granularity, and converting gradation. After the image processing, the X-ray image is displayed on a monitor or stored in a memory.

If the configuration of the X-ray sensor unit is such that the above described correction processing of the sensor characteristics and the image processing, such as sharpening, granularity reduction, and gradation conversion are performed internally, it will increase a cost, heat generation, and size of the X-ray sensor unit.

On the other hand, if the configuration of the X-ray imaging system is such that the X-ray sensor unit outputs a captured X-ray image to the main control unit without processing it, and the main control unit performs the correction processing of the sensor characteristics and all the image processing, the cost, heat generation, and size of the X-ray sensor unit will not be increased. However, in this case, since the main control unit needs to perform the correction processing of the sensor characteristics, the main control unit needs to comprehend all of the image reception characteristics unique to the sensor, and a problem of inconsistency between the X-ray sensor unit and the main control unit may occur.

For example, if the X-ray sensor unit is replaced with another one, the main control unit needs to acquire the sensor characteristics of the new X-ray sensor unit in some way. Further, since the correction processing of the sensor characteristics is performed by the main control unit, offset data necessary in correcting the sensor characteristics needs to be transferred from the X-ray sensor unit at the time the image is captured. This causes increase in communication traffic volume. Since the X-ray sensor unit and the main control unit are often located some distance apart, the increase in the communication traffic volume will be a major problem.

Regarding the image processing performed by the main control unit of the subsequent stage, in some cases, a parameter used for image adjustment changes according to a type of the captured image (e.g., imaging portion). In order to automatically adjust an image quality to a level appropriate for the diagnosis, it is necessary to analyze the captured image and determine the parameter.

FIGS. 8A and 8B are schematic diagrams illustrating an example of a gradation conversion curve used in general gradation conversion processing. In FIGS. 8A and 8B, a mean pixel value (also called a pixel mean value) of an image is calculated as a gradation conversion parameter (gradation conversion curve) illustrated in FIG. 8A. Then, the gradation conversion curve illustrated in FIG. 8A is shifted so that an input reference value (focus of attention) illustrated in FIG. 8B is maintained at a predetermined luminance value (output designated value) on a display monitor. The pixel value of the captured image is shifted (performed gradation conversion) according to the shifted gradation conversion curve. A method for such gradation conversion processing is discussed, for example, in Japanese Patent Application Laid-Open No. 2001-325594.

On the other hand, if the correction processing of the sensor characteristics is performed by the X-ray sensor unit, transmission of the data which is used in correcting the image to the main control unit will be unnecessary. This is advantageous from the viewpoint of a communication band. Further, the main control unit does not need to acquire the characteristics unique to the X-ray sensor unit, and the consistency between the X-ray sensor unit and the main control unit can be improved. Furthermore, since a load of the main control unit can be reduced, causing the X-ray sensor unit to perform the correction processing is also effective from the viewpoint of load sharing.

As described above, the configuration of the X-ray imaging system where the X-ray sensor unit transmits the image data to the main control unit after performing correction processing of the sensor characteristics, and where the main control unit performs image processing so that the image is appropriate for diagnosis brings about significant advantages.

However, according to the above described configuration where the X-ray sensor unit performs correction processing of the sensor characteristics and outputs the corrected image data to the main control unit, the X-ray sensor unit needs to temporally store pixel value data for one image therein for performing the correction processing of the sensor characteristics. In this case, since the image data is transmitted to the main control unit after the correction processing of the sensor characteristics is performed on the stored image data, delay may cause in the transmission of the image data to the main control unit. Further, since the main control unit also needs pixel value data of one image in calculating the pixel mean value of the image data, the main control unit needs to receive the image data for one image from the X-ray sensor unit and temporally store it.

FIG. 9 is a timing chart of a conventional example of a series of operations in the X-ray imaging, from X-ray irradiation to an object to display of the X-ray image.

According to the example illustrated in FIG. 9, after the main control unit receives all pixel data of one image, it calculates the pixel mean value as a gradation conversion parameter according to image analysis. Then, the image data which has been subjected to the image processing using the gradation conversion parameter is transmitted to the display monitor to be output. Thus, the time necessary in transferring the image data from the X-ray sensor unit to the main control unit may be a bottleneck, and delay time that occurs in the display of the image may be considered as a major inconvenience to the user.

The X-ray sensor unit developed in recent years can process images with finer definition. A pixel matrix of a general digital X-ray sensor unit is a few thousands×a few thousands (e.g., 2000×2000) pixels. Data for one pixel is about 8 to 16 bits. Thus, it is necessary to transfer large quantities of data. Further, in capturing a moving image, a real time image display is desired. Thus, if display of the image is considerably delayed, a difference between the operation and visual recognition will increase and will cause additional inconveniences.

Under such circumstances, in reducing the delay in the image display, it is necessary to improve a data transfer rate by increasing the number of bits transferred in a data transfer path or increasing a speed of data transfer. However, in increasing the bit numbers, a large diameter cable will be necessary. If such a cable is used, portability will be decreased. On the other hand, in increasing the data transfer speed, costs of components used in an input/output (I/O) unit will be increased and, further, securing a transmission quality will be difficult.

Further, as a method for preventing occurrence of the delay in the display, the main control unit can give priority to the display of the image. In such a case, after receiving the image data from the X-ray sensor unit, the main control unit may perform the image analysis such as calculation of the pixel mean value in parallel with the image processing such as gradation conversion.

FIG. 10 is a timing chart of a conventional example of a series of operations in the X-ray imaging when the display of image is prioritized, from X-ray irradiation to an object to display of the X-ray image.

According to the example illustrated in FIG. 10, image processing necessary in displaying the image is performed during the image analysis, so that the display of the image is prioritized and the delay in the display is prevented or at least minimized. In this case, a parameter obtained from the image analysis is reflected to the image processing of a next frame or later. For example, if an "i" frame is necessary in calculating an analysis parameter, the image processing of an "N"-th frame uses an analysis parameter of an image of an "N−i"-th frame. Similarly, the analysis parameter of the image of the "N"-th frame is reflected to the image processing of an "N+i"-th frame.

However, according to this method, the parameter obtained from an analysis result such as the pixel mean value cannot be reflected to the image processing in the frame at that time. In other words, the parameter is reflected after one frame or more. Thus, it is difficult to accurately process the image according to the analysis result.

Further, in imaging of an X-ray moving image, an irradiation amount of the X-ray is automatically adjusted at real time so that an optimum image for diagnosis is provided. According to this X-ray control, for example, if luminance of the whole X-ray image is low, the irradiation amount of the X-ray is increased, and if the luminance of the whole X-ray image is high, the irradiation amount of the X-ray is decreased. In this way, feedback of the X-ray control parameter which is calculated according to the image analysis is performed, and the irradiation of the X-ray is controlled according to the value. In this case, the pixel mean value, for example, is used as the X-ray control parameter.

Thus, in calculating the X-ray control parameter, the main control unit performs image analysis such as the calculation of the pixel mean value after receiving all the pixel data of one image, and then transmits the calculated X-ray control parameter to the X-ray generating apparatus. Thus, the time necessary in the image data transfer becomes a bottleneck, and the delay in the X-ray control may be increased or the reflection of the X-ray control parameter may be delayed a few frames.

SUMMARY OF THE INVENTION

The present invention has been made in consideration of the above situation, and has as its object to allow a main control unit to efficiently perform image processing such as gradation conversion while preventing delay in display of a radiation image or delay in radiation control.

According to the present invention, the foregoing object and other advantageous results are attained by providing a radiation imaging system that includes a radiation sensor unit configured to generate a radiation image based on a radiation ray that passes through an object and a main control unit configured to control acquisition of the radiation image. The radiation sensor unit includes, a radiation sensor that detects the radiation image based on the radiation ray that passes through the object, a sensor characteristics correction unit that performs sensor characteristics correction on the radiation image based on image reception characteristics of the radiation sensor, an image analysis unit that analyzes the radiation image in which the sensor characteristics correction has been performed by the sensor characteristics correction unit and calculates an analysis parameter, and a transmission unit that transmits the analysis parameter as a gradation conversion parameter and the radiation image which has been subjected to the sensor characteristics correction to the main control unit. The main control unit includes, a reception unit that receives the gradation conversion parameter and the radiation image which has been subjected to the sensor characteristics correction, and a gradation conversion processing unit that performs gradation conversion processing on the radiation image which has been subjected to the sensor characteristics correction using the gradation conversion parameter.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 3 is a flowchart illustrating an example of processing procedures of gradation conversion parameter (pixel mean value) calculation processing performed by an X-ray sensor unit illustrated in FIG. 1.

FIGS. 4A and 4B are flowcharts illustrating an example of processing procedures performed by the X-ray sensor unit illustrated in FIG. 1 and an example of processing procedures performed by a main control unit according to the first exemplary embodiment.

DESCRIPTION OF THE EMBODIMENTS

Various exemplary embodiments, features, and aspects of the invention will be described in detail below with reference to the drawings.

In the exemplary embodiments of the present invention described below, an X-ray imaging system using X-ray, which is one type of radiation rays, is used as an example of a radiation imaging system according to the present invention. The radiation imaging system of the present invention, however, is not limited to the X-ray imaging system and, for example, a radiation imaging system using a different radiation ray such as alpha ray, beta ray, or gamma ray may also be used. Further, although the X-ray imaging system is used as the radiation imaging system in the exemplary embodiment of the present invention described below, for example, a radiation imaging apparatus of an X-ray imaging apparatus may also be used.

A first exemplary embodiment of the present invention will be described.

Figure 1:
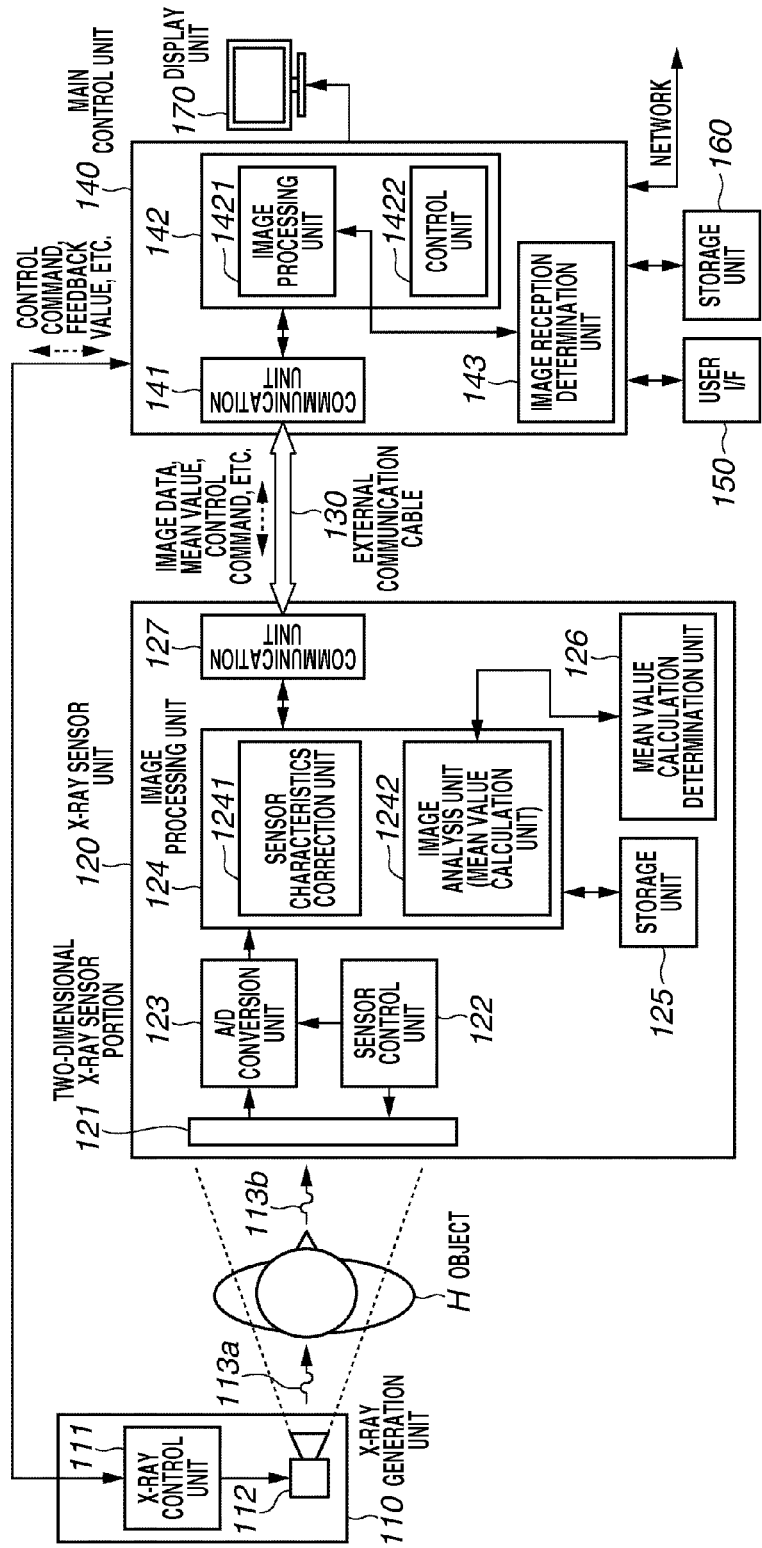
FIG. 1 is a schematic diagram illustrating an example of a configuration of an X-ray imaging system (radiation imaging system) according to a first exemplary embodiment of the present invention.

FIG. 1 is a schematic diagram illustrating an example of configuration of an X-ray imaging system (radiation imaging system) according to the first exemplary embodiment of the present invention.

As illustrated in FIG. 1, an X-ray imaging system 100 includes an X-ray generation unit 110, an X-ray sensor unit 120, an external communication cable 130, a main control unit 140, a user interface (I/F) 150, a storage unit 160, and a display unit 170.

The X-ray sensor unit (radiation sensor unit) 120 is connected to the main control unit 140 via the external communication cable 130. In other words, according to the X-ray imaging system 100 of the present exemplary embodiment, the main control unit 140 and the X-ray sensor unit 120 are configured as separate units. The main control unit 140 is, for example, a general-purpose computer such as a personal computer or the like that is specifically configured to control the X-ray sensor unit 120 and any peripheral devices thereof. The main control unit 140 is connected to, for example, the user I/F 150 which instructs X-ray imaging, the storage unit 160 which includes such as a read-only memory (ROM) or a hard disk, an output device such as the display unit 170 (e.g., a monitor or a printing device that displays the X-ray image), and a network connected to an external apparatus.

The X-ray generation unit (radiation generation unit) 110 irradiates an object H with an X-ray 113a which is one type of radiation rays according to a control of the main control unit 140. The X-ray generation unit 110 includes an X-ray control unit (radiation control unit) 111 and an X-ray source (radiation source) 112. The X-ray control unit 111 controls the X-ray 113a emitted from the X-ray source 112 according to the control of the main control unit 140. According to the control of the X-ray control unit 111, the X-ray source 112 irradiates the object H with the X-ray 113a. Thus, the X-ray generation unit 110 is configured such that the object H is exposed to the X-ray 113a and an irradiation amount of the X-ray is controllable.

The X-ray sensor unit 120 includes a two-dimensional X-ray sensor portion (two-dimensional radiation sensor portion) 121, a sensor control unit 122, an A/D conversion unit 123, an image processing unit 124, a storage unit 125, a mean value calculation determination unit 126, and a communication unit 127.

The two-dimensional X-ray sensor portion 121 detects an X-ray 113b that is emitted from the X-ray generation unit 110 and passed through the object H as an electric signal (X-ray image signal). More specifically, the two-dimensional X-ray sensor portion 121 detects an intensity two-dimensional distribution of the X-ray 113b as an X-ray image signal. The sensor control unit 122 controls a drive circuit and a read-out circuit (e.g., sample-and-hold circuit, multiplexer, and amplifier) in the two-dimensional X-ray sensor portion 121. The A/D conversion unit 123 converts an analog electric signal (X-ray image signal) read out from the two-dimensional X-ray sensor portion 121 into a digital signal, and outputs the digital signal as X-ray image data (radiation image data).

The image processing unit 124 performs image processing on the X-ray image data output from the A/D conversion unit 123. The image processing unit 124 includes a sensor characteristics correction unit 1241 and an image analysis unit (mean value calculation unit) 1242. The sensor characteristics correction unit 1241 corrects image reception characteristic (sensor characteristic) unique to the two-dimensional X-ray sensor portion 121. The image analysis unit (mean value calculation unit) 1242 analyzes the X-ray image data and calculates the pixel mean value as an analysis parameter. More specifically, according to the present exemplary embodiment, the analysis parameter will be used as a gradation conversion parameter for the gradation conversion processing performed by the main control unit 140.

The storage unit 125 stores the X-ray image data output from the A/D conversion unit 123 and the X-ray image data which has been subjected to the image processing performed by the image processing unit 124. The mean value calculation determination unit 126 determines whether each piece of pixel data of the X-ray image data is an object to be calculated a mean value. The communication unit 127 communicates with the main control unit 140 via the external communication cable 130.

The external communication cable 130 connects the X-ray sensor unit 120 (the communication unit 127) and the main control unit 140 (a communication unit 141) so that they can communicate with each other. To that end, it should be noted that the external communication "cable" 130 may not necessarily include a cable per se. As long as a communication link between the X-ray sensor unit 120 and the main control unit 140 can be established, any wired of wireless link known to a person of ordinary skill in the art can be used as the external communication cable 130.

The main control unit 140 comprehensively controls operations of the X-ray imaging system 100. The main control unit 140 includes the communication unit 141, a processing/control unit 142, and an image reception determination unit 143.

The communication unit 141 communicates with the X-ray sensor unit 120 via the external communication cable 130. The processing/control unit 142 includes an image processing unit 1421 and a control unit 1422. The image processing unit 1421 performs image processing, for example, sharpening, granularity reduction, noise reduction, and gradation conversion, as needed on the X-ray image data transmitted from the X-ray sensor unit 120.

The control unit 1422 comprehensively controls operations of the X-ray imaging system 100. For example, the control unit 1422 controls the two-dimensional X-ray sensor portion 121 and gives an instruction to the X-ray control unit 111 as well as controls the main control unit 140. The image reception determination unit 143 determines whether the X-ray image data transmitted from the X-ray sensor unit 120 has been received.

The user I/F 150 is operated by a user when the user gives various instructions concerning the X-ray imaging to the main control unit 140. The storage unit 160 stores, for example, the X-ray image data processed by the image processing unit 1421. The display unit 170 displays an X-ray image (image for diagnosis) based on the X-ray image data processed by the image processing unit 1421 and various types of information according to the control of the control unit 1422.

The main control unit 140 can output the X-ray image data to a printer via a network or transfer the X-ray image data to a remote diagnosis system or an image management system via a network.

The external communication cable 130 that connects the X-ray sensor unit 120 and the main control unit 140 is used not only for the communication of the X-ray image data but also for transmitting and receiving a command for controlling the X-ray sensor unit 120 or a command for indicating a state of the X-ray sensor unit 120. For example, a command for specifying an imaging frame rate or binning and a synchronization signal that indicates an operating state of the two-dimensional X-ray sensor portion 121 may be transmitted via the external communication cable 130. In the present exemplary embodiment, although the communication is described as performed by one external communication cable 130, command communication, image data communication, and synchronization signal communication can be performed using different communication cables.

Next, an inner configuration of the two-dimensional X-ray sensor portion 121 illustrated in FIG. 1 will be described.

Figure 2:
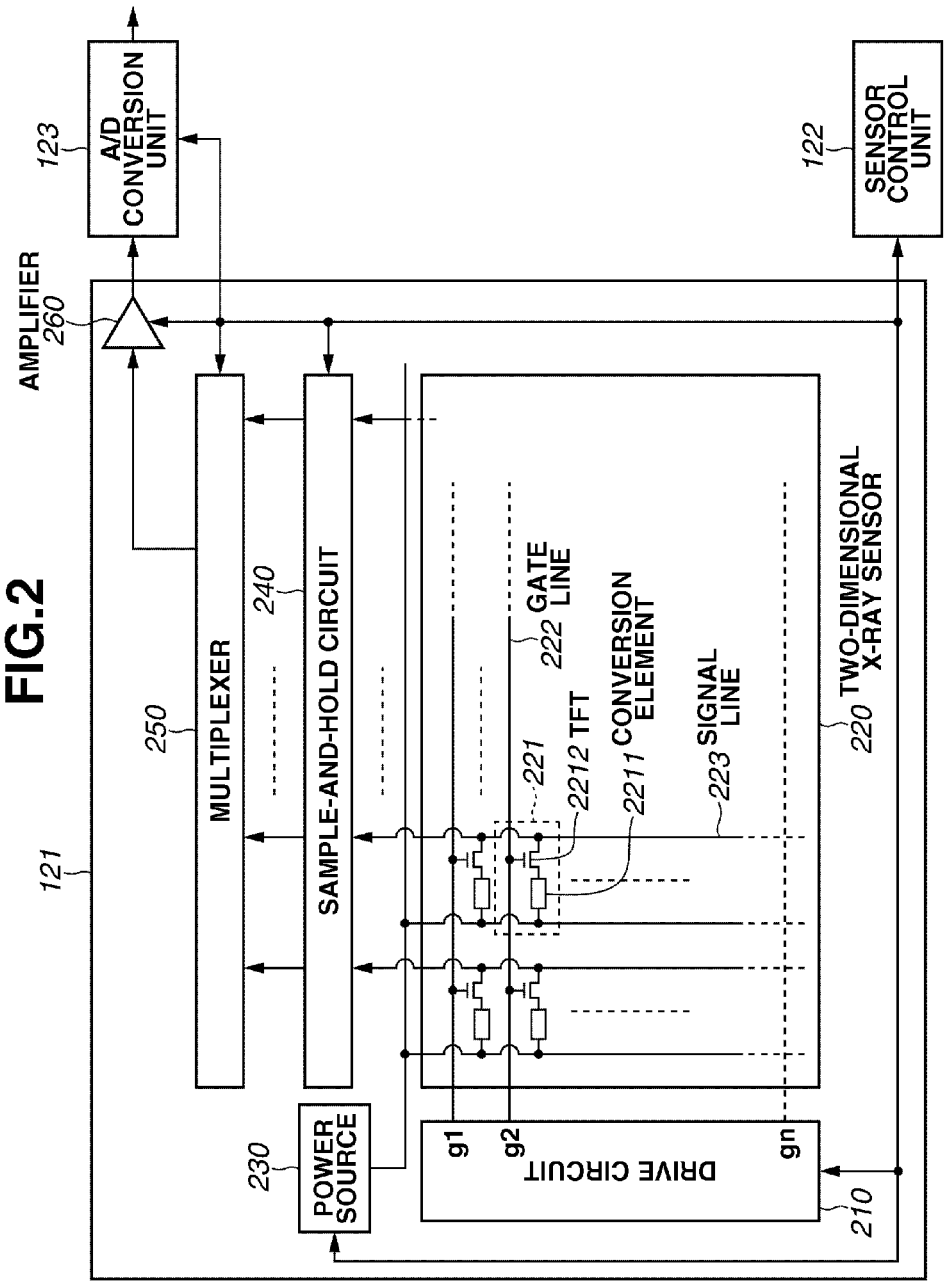
FIG. 2 is a schematic diagram illustrating an example of an inner configuration of a two-dimensional X-ray sensor portion illustrated in FIG. 1.

FIG. 2 is a schematic diagram illustrating an example of the inner configuration of the two-dimensional X-ray sensor portion 121 illustrated in FIG. 1. In FIG. 2, in addition to the inner configuration of the two-dimensional X-ray sensor portion 121 in FIG. 1, the sensor control unit 122 and the A/D conversion unit 123 in FIG. 1 are also illustrated.

As illustrated in FIG. 2, the two-dimensional X-ray sensor portion 121 includes a drive circuit 210, a two-dimensional X-ray sensor 220, a power supply 230, a sample-and-hold circuit 240, a multiplexer 250, and an amplifier 260.

The drive circuit 210, the power supply 230, the sample-and-hold circuit 240, the multiplexer 250, and the amplifier 260 are controlled by the sensor control unit 122.

In the two-dimensional X-ray sensor 220, pixels 221 each of which includes one conversion element 2211 and one TFT 2212 are arranged in a two-dimensional array (two-dimensional matrix). Further, the two-dimensional X-ray sensor 220 includes a plurality of gate lines 222 (drive lines) (gl to gn) each of which connects each of the pixels 221 in a row direction, and a plurality of signal lines 223 (read-out lines) each of which connects each of the pixels 221 in a column direction.

The conversion element 2211 converts an incident X-ray into an electric signal. The conversion element 2211 may include, for example, a phosphorous material that converts the incident X-ray into light and a photoelectric conversion element that converts the light into an electric signal. Alternatively, the conversion element 2211 may be configured of a component that directly converts the incident X-ray into an electric signal.

The drive circuit 210 simultaneously addresses a group of the pixels 221 of a certain row via a gate line 222 according to the control of the sensor control unit 122. According to this process, a charge (electric signal) accumulated in each pixel (each conversion element) of the row is read out by the sample-and-hold circuit 240 via a signal line 223 and stored in the sample-and-hold circuit 240. Then, the charge of the pixel 221 stored in the sample-and-hold circuit 240 is sequentially read out by the multiplexer 250, amplified by the amplifier 260, and transmitted to the A/D conversion unit 123. At the A/D conversion unit 123, the charge is converted into a digital signal (digital value).

Each time that the reading of the charges of the pixels 221 of each row is completed, the drive circuit 210 sequentially reads out the next row of the two-dimensional X-ray sensor 220. Accordingly, the charges of all the pixels 221 of the two-dimensional X-ray sensor 220 are finally read out and the X-ray image data is generated.

Next, the X-ray image data converted into the digital value is stored in a frame memory in the storage unit 125 illustrated in FIG. 1. Then, the image processing of the image data is performed by the sensor characteristics correction unit 1241 to correct the image reception characteristics unique to the sensor such as stationary noise and variation in sensitivity characteristics.

The sensor characteristics correction unit 1241 mainly performs sensor characteristics correction such as offset correction, gain correction, and defective pixel correction. The correction processing performed by the sensor characteristics correction unit 1241 is described below.

If an image is read out in a state where the X-ray is not being emitted, the output value is not always "0" and an offset component is added to the value. In order to correct the offset component, the two-dimensional X-ray sensor portion 121 stores image data which is obtained in a state where the X-ray is not emitted as offset image data (reference image data) therein (e.g., in the storage unit 125). Then, the sensor characteristics correction unit 1241 performs the offset correction processing on the X-ray image data by using a difference between the pixel value of the X-ray image data obtained by the X-ray imaging and the pixel value of the offset image data.

The above described offset component varies according to the frame. As a method for preventing the variation from occurring, for example, immediately after the X-ray imaging, the above described two-dimensional X-ray sensor 220 is read out in a state where the X-ray is not emitted, and the read image data is stored, for example, in the storage unit 125 as the offset image data. At this time, the offset image data is stored in a region of an offset image memory which is different from the frame memory in which the X-ray image data obtained by the X-ray imaging is stored.

Then, by using a difference between the X-ray image data stored in the frame memory and the offset image data stored in the offset image memory, the sensor characteristics correction unit 1241 acquires offset-corrected X-ray image data. By performing this processing for each frame, the variation of the offset component can be prevented.

Although the offset image data is acquired each time immediately after the X-ray imaging in the following description, the acquisition of the offset image data of the present exemplary embodiment is not limited to such processing. For example, the offset image data can be acquired just before the X-ray imaging. Further, if the variation of the offset component between the frames is small, offset correction of a plurality of X-ray images can be performed by using one piece of offset image data prepared in advance.

The sensor characteristics correction unit 1241 performs gain correction in order to correct the variation in sensitivity of the pixel 221 of the two-dimensional X-ray sensor 220 with respect to the offset-corrected X-ray image data. Then, the sensor characteristics correction unit 1241 corrects the defective pixel. According to the above described sensor characteristics correction processing, X-ray image data which has been subjected to the sensor characteristics correction can be obtained.

The sensor characteristics correction processing performed by the sensor characteristics correction unit 1241 is not limited to the above described offset correction, gain correction, and the defective pixel correction. For example, the processing can include processing for correcting moire (grid stripes) that is produced by a grid used for suppressing scattered radiation. Further, the sensor characteristics correction unit 1241 may perform only some of the above described processing such as only the offset correction and the gain correction. However, it is desirable that the sensor characteristics correction processing at least includes the offset correction.

According to the present exemplary embodiment, the image analysis of the X-ray image data is performed by the image analysis unit (mean value calculation unit) 1242, and the pixel mean value which is used as a gradation conversion parameter in the gradation conversion processing performed by the main control unit 140 is calculated.

Although the pixel mean value is used as the gradation conversion parameter, in the following description, a minimum value, a maximum value, or a median value of a result of a histogram analysis of the X-ray image data or a particular pixel value can be used as the gradation conversion parameter to determine a gradation conversion condition.

Now, a calculation method of the above described pixel mean value will be described.

First, the image analysis unit (mean value calculation unit) 1242 reads out the pixel data of the X-ray image data from the frame memory of the storage unit 125. Then, the mean value calculation determination unit 126 determines whether the read pixel data is pixel data of a pixel which is a mean value calculation object. The pixel which is determined as the calculation object is considered as a pixel in an X-ray radiation field region.

At this time, information about the radiation field region is acquired from, for example, an external apparatus that has position information about a collimator (not shown) and includes information about which address range is in the radiation field region. For example, if the collimator is a rectangular collimator, information such as a central coordinate of the collimator and distances from top to bottom and from right to left will be received from the collimator or the main control unit 140 via the external communication cable 130.

Then, the mean value calculation determination unit 126 stores information about the address of the frame memory that corresponds to the pixel in the radiation field region from the received information, and determines whether the address of the pixel whose image data has been read out is in an address range of the radiation field region. Then, the image analysis unit (mean value calculation unit) 1242 calculates the pixel mean value using the image data of the pixel which is determined as the mean value calculation object by the mean value calculation determination unit 126.

FIG. 3 is a flowchart illustrating an example of processing procedures of the gradation conversion parameter (pixel mean value) calculation processing performed by the X-ray sensor unit 120 illustrated in FIG. 1.

In step S101, the image analysis unit (mean value calculation unit) 1242 sets a value of a counter to zero.

In step S102, the image analysis unit (mean value calculation unit) 1242 reads out the pixel data of the X-ray image data from the frame memory of the storage unit 125.

In step S103, the mean value calculation determination unit 126 determines whether the pixel data read out in step S102 is data of a pixel which is the mean value calculation object using the above described radiation field region information.

More specifically, according to the present exemplary embodiment, a pixel in the radiation field region is considered as the pixel of the mean value calculation object.

As a result of the determination in step S103, if the pixel data read out in step S102 is the pixel data of the pixel of the mean value calculation object (YES in step S103), the processing proceeds to step S104.

In step S104, the image analysis unit (mean value calculation unit) 1242 adds the pixel value based on the pixel data read out in step S102 to a value of the mean value calculation memory provided in the storage unit 125. Although the mean value calculation memory is provided in the storage unit 125 according to the present exemplary embodiment, the mean value calculation memory is not limited to such an example. For example, it can be provided in the image analysis unit (mean value calculation unit) 1242 as an internal memory. Then, the image analysis unit (mean value calculation unit) 1242 increments the counter value by one.

If the processing in step S104 is completed, or in step S103, if the pixel data read out in step S102 is determined as not the pixel data of the pixel of the mean value calculation object (NO in step S103), the processing proceeds to step S105.

In step S105, the image analysis unit (mean value calculation unit) 1242 determines whether the determination processing is completed for all of the pixels of the X-ray image data stored in the frame memory of the storage unit 125.

As a result of the determination in step S105, if the determination processing is not yet completed for all the pixels of the X-ray image data (in other words, a pixel which is not subjected to the determination processing exists) (NO in step S105), then the processing returns to step S102. In step S102, the image analysis unit (mean value calculation unit) 1242 reads out the pixel data which is not yet subjected to the determination processing, and then the processing in step S103 and later will be performed again.

On the other hand, as a result of the determination in step S105, if the determination processing is completed for all the pixels of the X-ray image data (YES in step S105), the processing proceeds to step S106. In this case, a result value of the addition of the pixel values of the pixels of the mean value calculation object (i.e., pixels in the radiation field region) is stored in the mean value calculation memory.

In step S106, the image analysis unit (mean value calculation unit) 1242 calculates the pixel mean value which will be used as the gradation conversion parameter by dividing the result value of the addition processing stored in the mean value calculation memory by the counter value.

When the processing in step S106 is completed, the processing of the flowchart in FIG. 3 ends.

When the pixel data of the next frame is read out, the processing of the flowchart in FIG. 3 will be repeated. In this case, the counter value and the value stored in the mean value calculation memory will be cleared (initialized) before the processing is started.

The calculation processing of the pixel mean value illustrated in FIG. 3 is performed when the pixel data of the X-ray image data is read from the frame memory during or after the correction processing of the sensor characteristics by inputting the pixel data in the image analysis unit (mean value calculation unit) 1242.

Although the pixel mean value is calculated using the pixels in the X-ray radiation field region, the pixel mean value of the present exemplary embodiment can be obtained from pixels in other regions. For example, it can be obtained from the whole image or from a region in the radiation field region but excluding the region where the X-ray is directly applied to the two-dimensional X-ray sensor portion 121 without passing through the object H, or from a region excluding a metal region.

Then, the X-ray sensor unit 120 transmits the X-ray image data, which has been subjected to the sensor characteristics correction and internally generated, and the gradation conversion parameter (pixel mean value) to the main control unit 140 via the external communication cable 130. Then, the image processing unit 1421 of the main control unit 140 performs image processing, such as gradation conversion, of the received X-ray image data which has been subjected to the sensor characteristics correction according to the received gradation conversion parameter. Then, an X-ray image (image for diagnosis) based on the X-ray image data processed by the image processing unit 1421 is displayed on the display unit 170.

When the X-ray sensor unit 120 transmits the X-ray image data which has been subjected to the sensor characteristics correction from the communication unit 127, the X-ray sensor unit 120 divides the X-ray image data which has been subjected to the sensor characteristics correction into units of communication packets or into predetermined units, and then transmits the divided data to the main control unit 140. At that time, the X-ray sensor unit 120 embeds the gradation conversion parameter in the header of each piece of the divided image data and transmits the data to the main control unit 140.

Although the gradation conversion parameter (pixel mean value) is embedded in the header of the X-ray image data when the image data is transmitted in the description above, the transmission method of the gradation conversion parameter is not limited to such a method. For example, the gradation conversion parameter can be transmitted at the same time that the X-ray image data is transmitted to the main control unit 140 or earlier.

In other words, the gradation conversion parameter can be transmitted to the main control unit 140 as a different piece of communication data before the X-ray image data is transmitted to the main control unit 140. Further, in this case, the gradation conversion parameter and the X-ray image data which has been subjected to the sensor characteristics correction are not necessarily transmitted from the communication unit 127, and can be transmitted from different communication units.

In this case, the image reception determination unit 143 in the main control unit 140 determines whether the amount of data it has received is more than or equal to the minimum amount of data necessary for starting the image processing performed by the image processing unit 1421 using the gradation conversion parameter. If such pixel data has been received, the image processing unit 1421 starts the image processing such as the gradation conversion processing at once.

Next, the processing performed by the X-ray sensor unit 120 according to the present exemplary embodiment will be described.

Figure 4A:
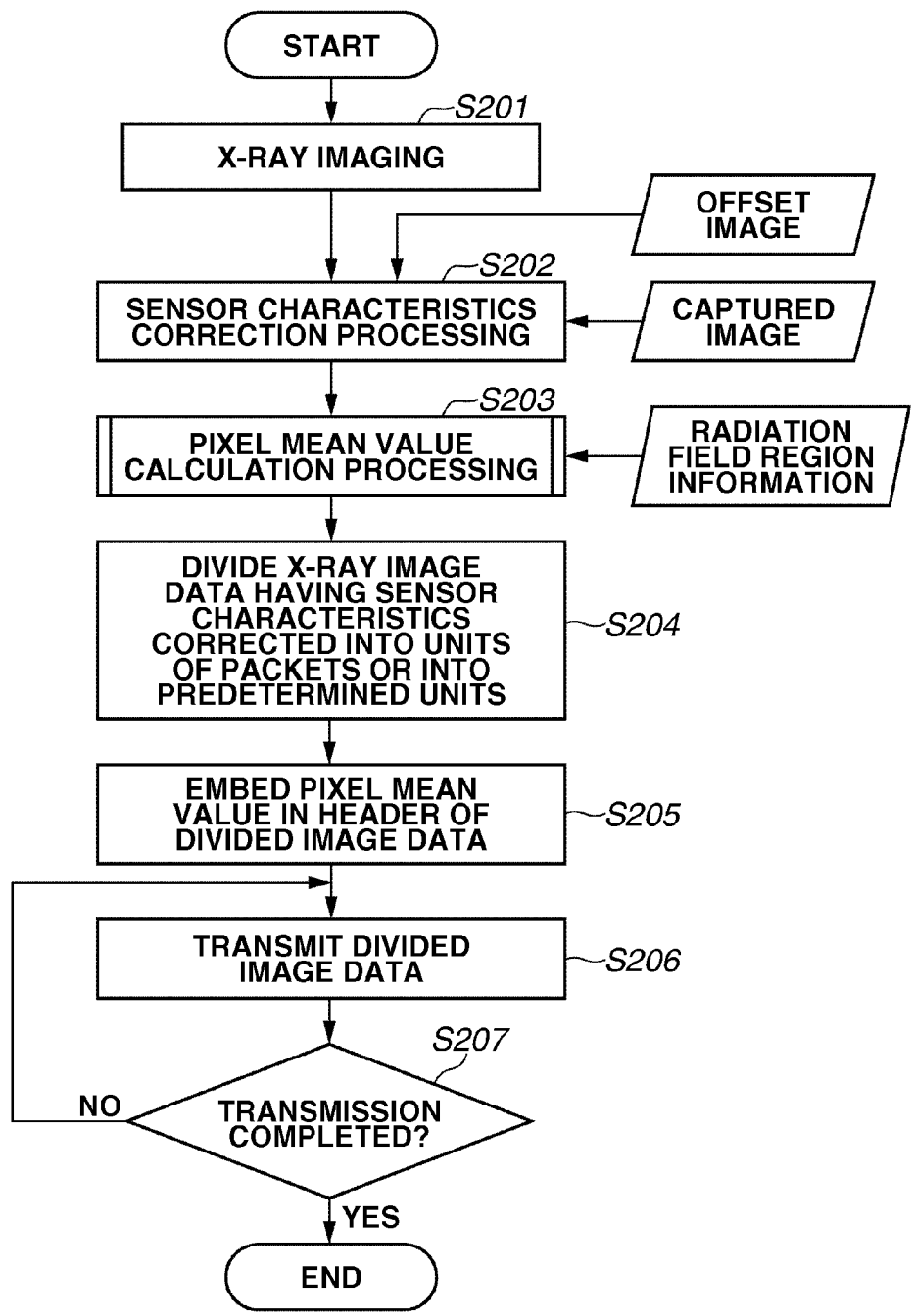

FIG. 4A is a flowchart illustrating the processing performed by the X-ray sensor unit 120 illustrated in FIG. 1 according to the first exemplary embodiment of the present invention.

In step S201, the X-ray sensor unit 120 performs the X-ray imaging of the object H. More specifically, the two-dimensional X-ray sensor portion 121 detects the X-ray 113b, which is the X-ray emitted from the X-ray generation unit 110 and passed through the object H, as an analog X-ray image signal. Then, the A/D conversion unit 123 converts the analog X-ray image signal read out by the two-dimensional X-ray sensor portion 121 into a digital signal, and outputs it as X-ray image data (captured image data).

The X-ray image data (captured image data) output from the A/D conversion unit 123 is stored in the frame memory of the storage unit 125 via the image processing unit 124. Further, before and/or after the X-ray imaging, the above described offset image data (reference image data) is acquired and stored in the offset image memory of the storage unit 125.

In step S202, the sensor characteristics correction unit 1241 performs the sensor characteristics correction processing on the X-ray image data (captured image data) stored in the frame memory with using the offset image data stored in the offset image memory. Then, the sensor characteristics correction unit 1241 performs the sensor characteristics correction processing on the pixel data of the X-ray image data (captured image data) read out from the frame memory with using the corresponding pixel data read out from the offset image memory.

For example, in step S202, the offset correction processing is performed by obtaining a difference between the X-ray image data (captured image data) and the offset image data. Then, the sensor characteristics correction unit 1241 performs various types of processing on the X-ray image data which has been subjected to offset correction as needed, generates the X-ray image data which has been subjected to the sensor characteristics correction, and stores the generated data in, for example, the frame memory of the storage unit 125.

In step S203, the image analysis unit (mean value calculation unit) 1242 reads out the X-ray image data which has been subjected to the sensor characteristics correction from the frame memory of the storage unit 125, for example, and calculates the pixel mean value which will be used as the gradation conversion parameter. Detailed processing in step S203 will be illustrated in the flowchart in FIG. 3.

In step S204, the communication unit 127 (or the image processing unit 124) divides the X-ray image data which has been subjected to the sensor characteristics correction into units of communication packets or into predetermined units and generates divided image data.

In step S205, the communication unit 127 converts the format of the divided image data into a data format for communication and also embeds the pixel mean value obtained in step S203 in the header of each piece of the divided image data.

In step S206, the communication unit 127 transmits the divided image data in which the pixel mean value has been embedded in the header to the communication unit 141 of the main control unit 140 via the external communication cable 130. The communication unit 127 that performs the processing in step S206 configures the transmission unit.

In step S207, the communication unit 127 determines whether the transmission of all pieces of the divided image data has been completed.

As a result of the determination in step S207, if the divided image data which has not been transmitted yet (untransmitted divided image data) exists (NO in step S207), the processing returns to step S206, and the transmission processing of such data will be performed.

On the other hand, as a result of the determination in step S207, if transmission of all pieces of the divided image data is completed (YES in step S207), the processing of the flowchart in FIG. 4A ends.

Next, the processing performed by the main control unit 140 according to the present exemplary embodiment will be described.

FIG. 4B is a flowchart illustrating an example of processing performed by the main control unit 140 illustrated in FIG. 1 according to the first exemplary embodiment of the present invention.

In step S301, the communication unit 141 receives the divided image data of the X-ray image data which has been subjected to the sensor characteristics correction and divided into units of communication packets or into predetermined units. The communication unit 141 which performs the process of receiving the divided image data, in step S301, is configured as the reception unit.

In step S302, the image reception determination unit 143 determines whether the image data received is more than or equal to the minimum amount of data necessary for starting the image processing performed by the image processing unit 1421 using the gradation conversion parameter (pixel mean value).

As a result of the determination in step S302, if the data received is less than the minimum amount of data necessary for starting the image processing (NO in step S302), the processing returns to step S301, and the reception processing of the divided image data will be repeated.

On the other hand, as a result of the determination in step S302, if the data received is more than or equal to the minimum amount of data necessary for starting the image processing (YES in step S302), the processing proceeds to step S303.

In step S303, the image processing unit 1421 performs image processing such as gradation conversion processing according to the gradation conversion parameter (pixel mean value). The image processing unit 1421 that performs the gradation conversion processing, in step S303, is configured as the gradation conversion processing unit.

In step S304, the image processing unit 1421 determines whether the image processing is completed on all the pixels of the X-ray image data which has been subjected to the sensor characteristics correction.

As a result of the determination in step S304, if image processing is not completed yet on all the pixels of the X-ray image data which has been subjected to the sensor characteristics correction (an unprocessed pixel exists) (NO in step S304), then the processing returns to step S301.

On the other hand, as a result of the determination in step S304, if image processing is completed on all the pixels of the X-ray image data which has been subjected to the sensor characteristics correction (YES in step S304), the processing proceeds to step S305.

In step S305, the processing/control unit 142 stores the X-ray image (image for diagnosis) which is based on the X-ray image data processed by the image processing unit 1421 in the storage unit 160 and also displays the X-ray image on the display unit 170.

When the processing in step S305 ends, the processing of the flowchart in FIG. 4B ends.

As described above, since the correction processing of the sensor characteristics is performed on the side of the X-ray sensor unit 120 according to the present exemplary embodiment, the X-ray image data of one frame needs to be once stored in the frame memory of the storage unit 125 of the X-ray sensor unit 120. Thus, there are concerns about the delay in the transmission of the X-ray image data transmitted from the X-ray sensor unit 120 to the main control unit 140.

Thus, according to the present exemplary embodiment, the image analysis processing is performed in advance in the X-ray sensor unit 120. The pixel mean value which serves as the gradation conversion parameter is calculated, and the obtained pixel mean value is transmitted to the image processing unit 1421 of the main control unit 140 together with the divided image data or prior to the transmission of the divided image data. Then, upon receiving the image data which is more than or equal to the minimum amount of data necessary for starting the image processing using the pixel mean value, the image processing is started on the side of the main control unit 140.

At that time, since the main control unit 140 acquires the pixel mean value serving as the gradation conversion parameter from the header portion of the divided image data or prior to the transmission of the divided image data, image processing to which the gradation conversion parameter is reflected can be sequentially started.

Figure 5:
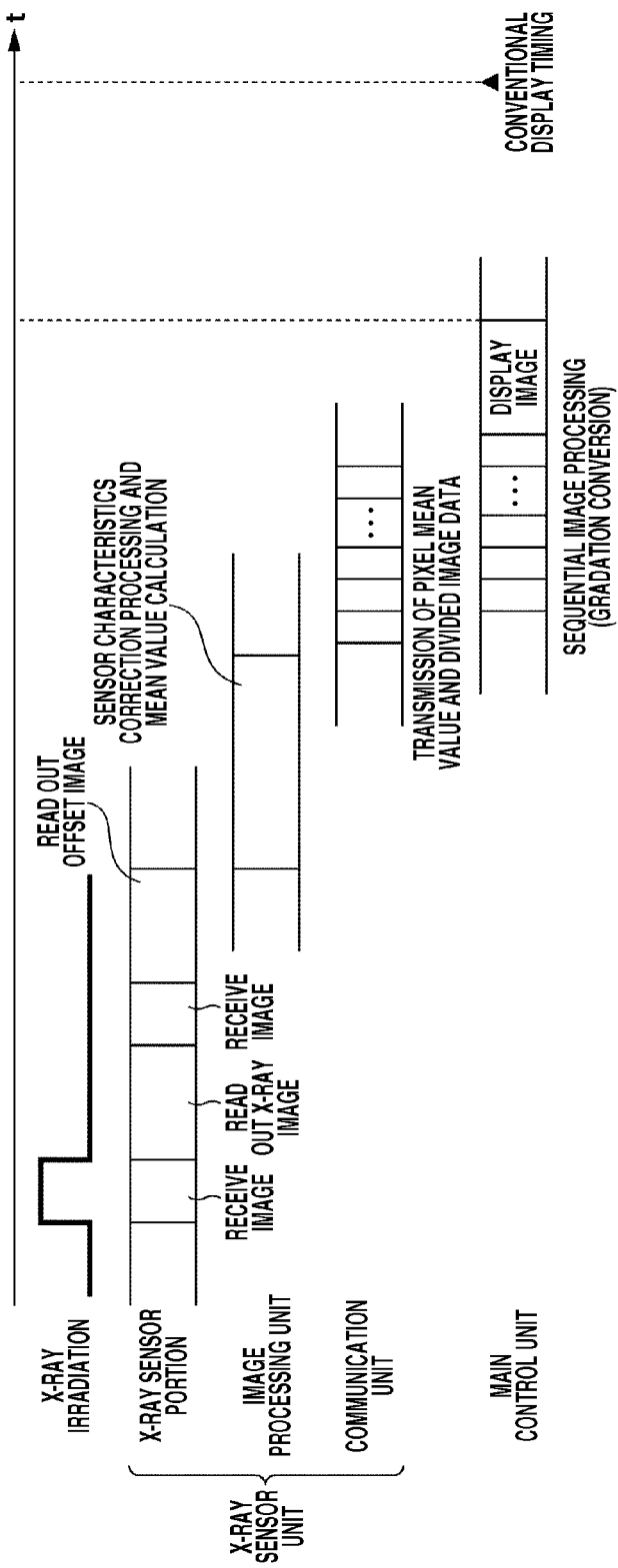
FIG. 5 is a timing chart illustrating an example of X-ray imaging processing according to the first exemplary embodiment.

FIG. 5 is a timing chart illustrating an example of the flow of the X-ray imaging according to the first exemplary embodiment of the present invention. FIG. 5 illustrates the timing of the processing from irradiation of the object H with an X-ray to the display of the X-ray image. Further, conventional display timing (timing indicated by a broken line in FIG. 9) is also illustrated in FIG. 5.

Figure 9:
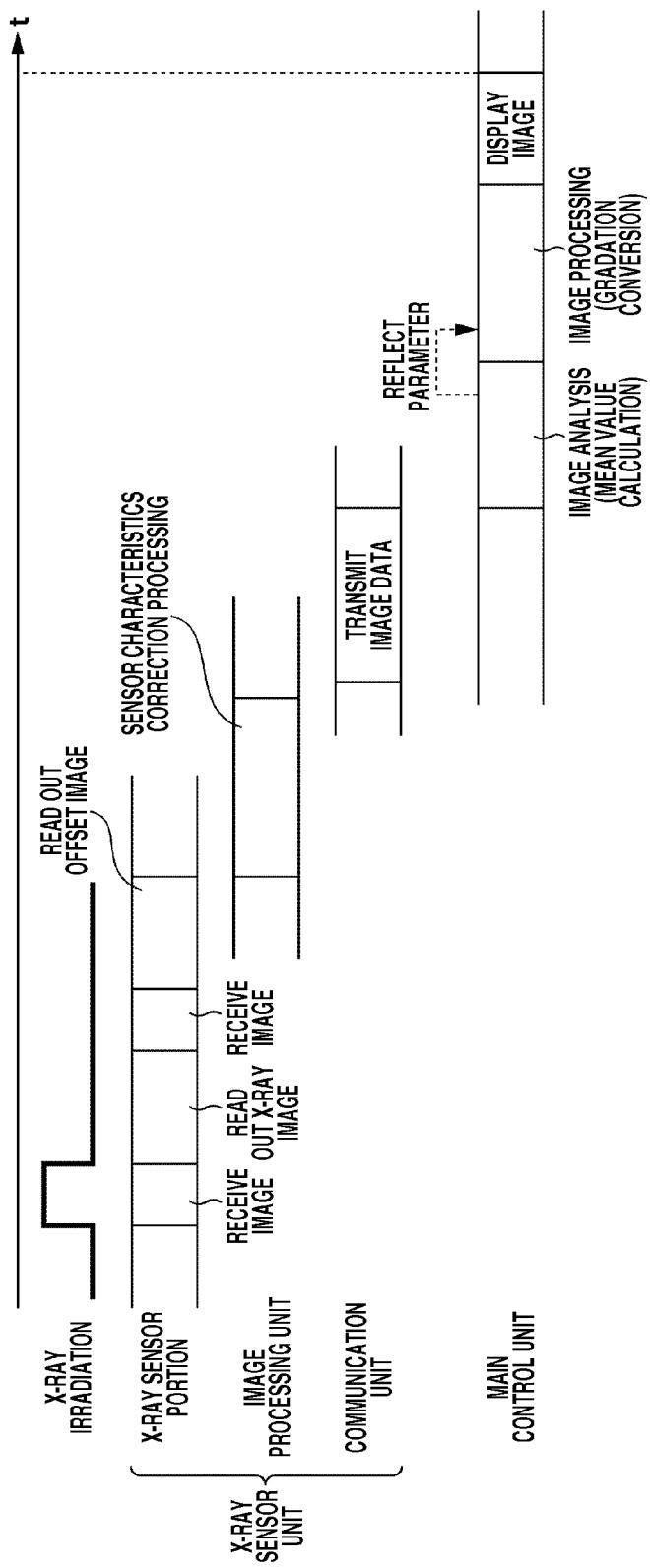
FIG. 9 is a timing chart illustrating an example of X-ray imaging processing according to a conventional technique.
Figure 10:
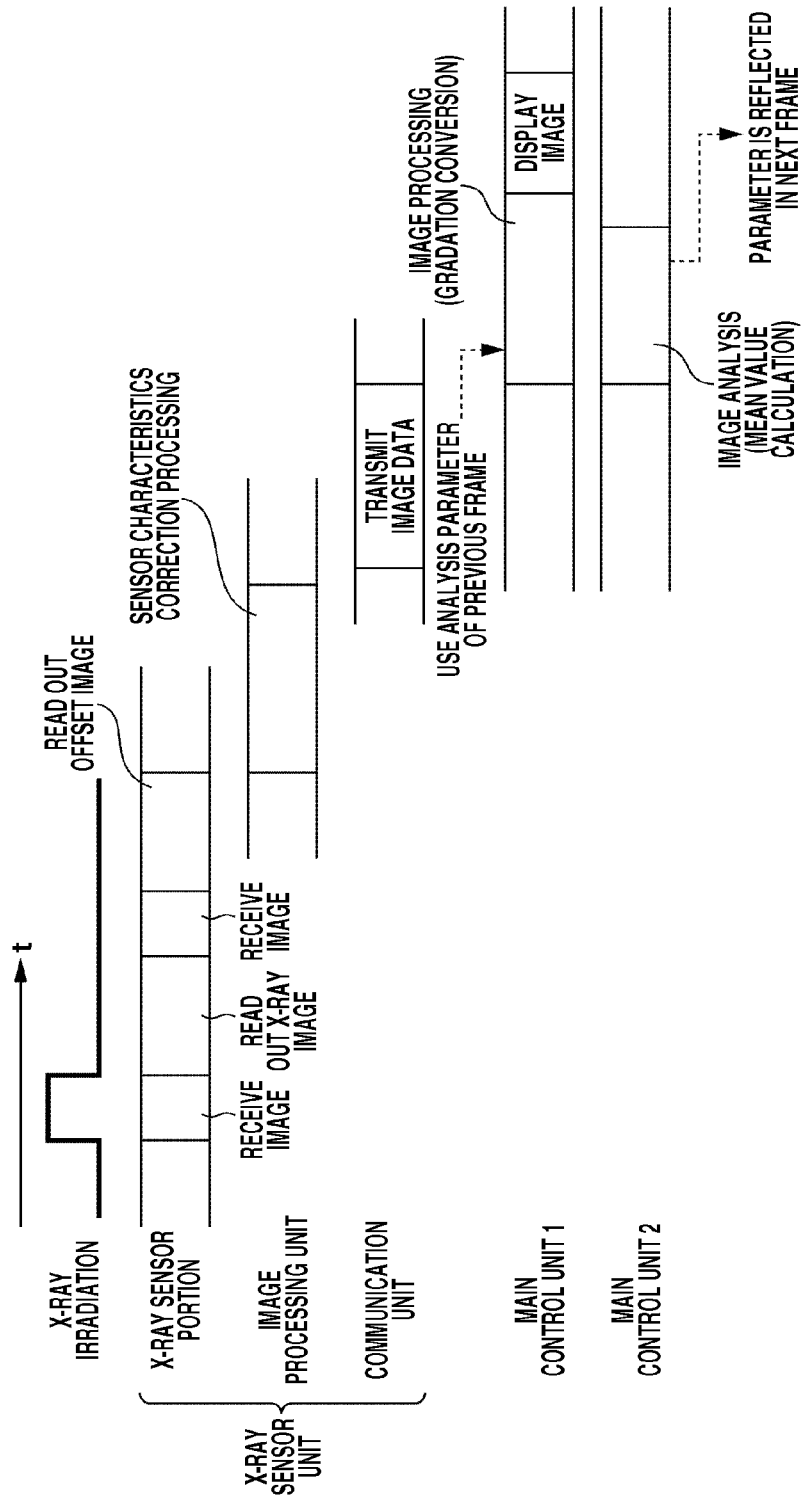
FIG. 10 is a timing chart illustrating an example of X-ray imaging processing where image display is given priority according to a conventional technique.

Compared to the conventional case illustrated in FIG. 9 in which the image analysis is performed on the main control unit 140 side after receiving one frame of image data and then the image processing is performed using the obtained parameter, the image can be displayed at earlier timing in the present exemplary embodiment illustrated in FIG. 5. Accordingly, the delay in the display of the image can be improved. Further, according to the present exemplary embodiment, a parameter obtained from the image analysis can be used in the same frame. Thus, the delay that the parameter is used in the next or later frame does not occur.

Next, a second exemplary embodiment of the present invention will be described.

The configuration of the X-ray imaging system (radiation imaging system) according to the second exemplary embodiment is similar to that of the X-ray imaging system 100 illustrated in FIG. 1. More specifically, the X-ray sensor unit 120 and the main control unit 140 are connected via the external communication cable 130. The X-ray sensor unit 120 performs correction processing of the sensor characteristics and calculation processing of the pixel mean value relating to the gradation conversion parameter by image analysis, and transfers the obtained X-ray image data which has been subjected to the sensor characteristics correction and the pixel mean value to the main control unit 140. Then, the main control unit 140 performs the gradation conversion processing on the X-ray image data which has been subjected to the sensor characteristics correction using the pixel mean value as the gradation conversion parameter.

Further, the inner configuration of the two-dimensional X-ray sensor portion according to the second exemplary embodiment is similar to the inner configuration of the two-dimensional X-ray sensor portion 121 according to the first exemplary embodiment as illustrated in FIG. 2.

The calculation processing of the pixel mean value according to the first exemplary embodiment is based on the radiation field region relating to the radiation field region information obtained from the external apparatus such as the collimator or the main control unit.

On the contrary, according to the second exemplary embodiment, the X-ray image data is analyzed in the X-ray sensor unit 120 and then the radiation field recognition processing is performed. Then, by using a pixel in the radiation field region obtained from a recognition result as a pixel of the mean value calculation object, calculation processing of the pixel mean value of that pixel will be performed.

Various methods have been discussed for the radiation field recognition processing, and any method can be used in the present exemplary embodiment. For example, an outline of the radiation field region can be obtained from edge extraction of the image. Further, a distribution region in which luminance is low in a histogram of pixel distribution may be considered as a region out of the radiation field region.

Next, processing performed by the X-ray sensor unit 120 according to the present exemplary embodiment will be described.

Figure 6:
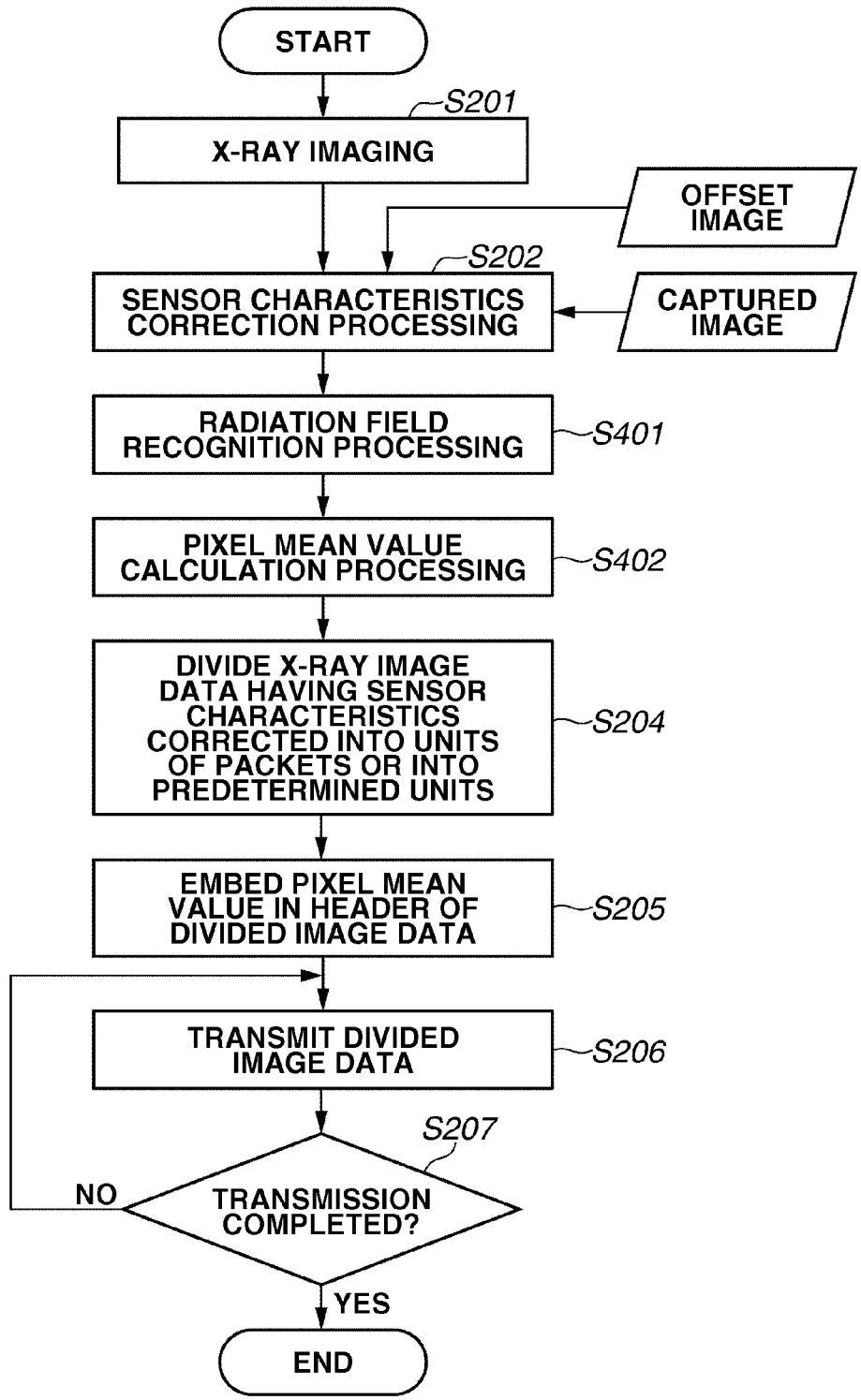
FIG. 6 is a flowchart illustrating an example of processing procedures performed by the X-ray sensor unit according to a second exemplary embodiment of the present invention.

FIG. 6 is a flowchart illustrating an example of processing procedures performed by the X-ray sensor unit 120 illustrated in FIG. 1 according to the second exemplary embodiment of the present invention. In FIG. 6, processing steps similar to those illustrated in FIG. 4A will be given the same step numbers and their descriptions are not repeated.

First, according to the processing in steps S201 and S202 in FIG. 4A, the X-ray image data which has been subjected to the sensor characteristics correction is acquired.

In step S401, the image analysis unit (mean value calculation unit) 1242 executes the radiation field recognition processing with respect to the X-ray image data which has been subjected to the sensor characteristics correction.

In step S402, the image analysis unit (mean value calculation unit) 1242 calculates a pixel mean value of pixel values of pixels in the radiation field region as pixels of a mean value calculation objects according to a result of the radiation field recognition obtained in step S401.

After the processing in steps S204 to S207 in FIG. 4A is completed, the processing of the flowchart in FIG. 6 ends.

Although the pixel mean value described above is calculated using the pixel in the X-ray radiation field region, the pixel mean value of the present exemplary embodiment can be obtained from other regions. For example, in addition to recognizing the radiation field by the image analysis, a region where the X-ray is directly applied to the two-dimensional X-ray sensor portion 121 without passing through the object H and a metal region can be recognized. Then, a pixel taken from a region excluding such regions can be used for calculating the mean value.

According to the present exemplary embodiment, recognition processing of the radiation field region is performed in the X-ray sensor unit 120, and the pixel mean value which is used as the gradation conversion parameter is calculated using the recognition result. Thus, the X-ray sensor unit 120 does not need to acquire the radiation field region information from an external apparatus. Further, by calculating the gradation conversion parameter (pixel mean value) in advance, the main control unit 140 in the subsequent stage can start the image processing using the gradation conversion parameter immediately after receiving the gradation conversion parameter. Accordingly, the delay in display of the X-ray image (image for diagnosis) can be prevented.

Next a third exemplary embodiment of the present invention will be described.

Figure 7:
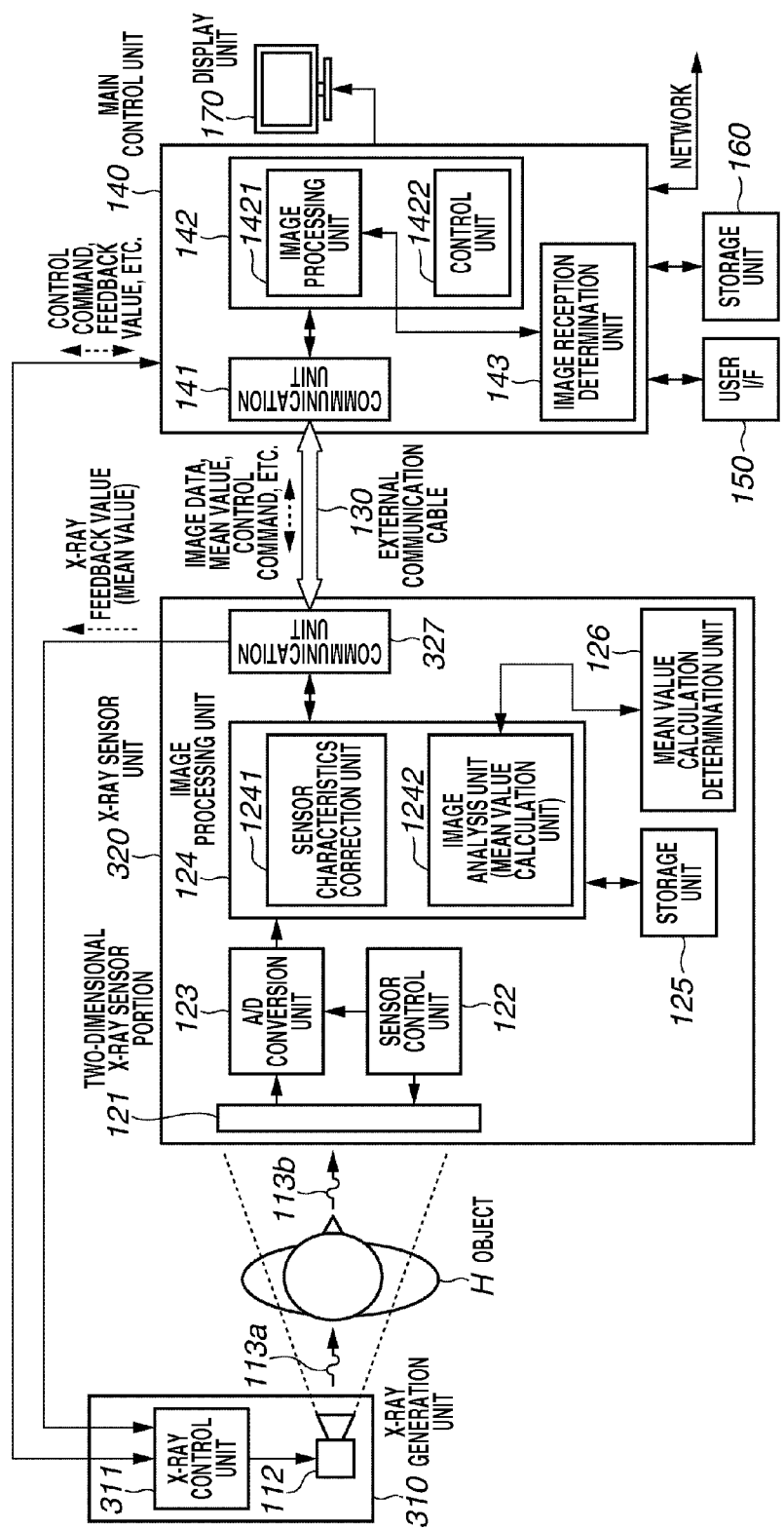
FIG. 7 is a schematic diagram illustrating an example of a configuration of the X-ray imaging system (radiation imaging system) according to a third exemplary embodiment of the present invention.
Figure 8B:
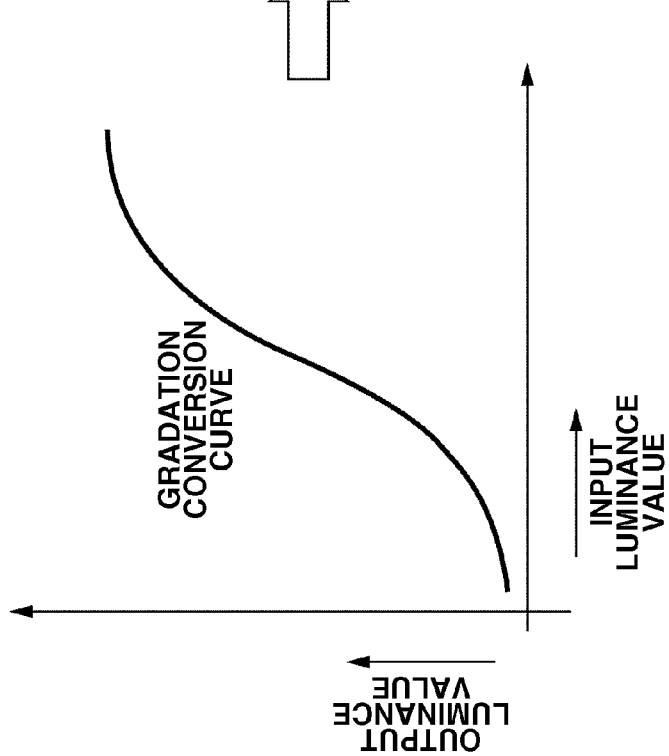
FIGS. 8A and 8B are schematic diagrams illustrating an example of change of a gradation conversion curve used in general gradation conversion processing.
Figure 8A:
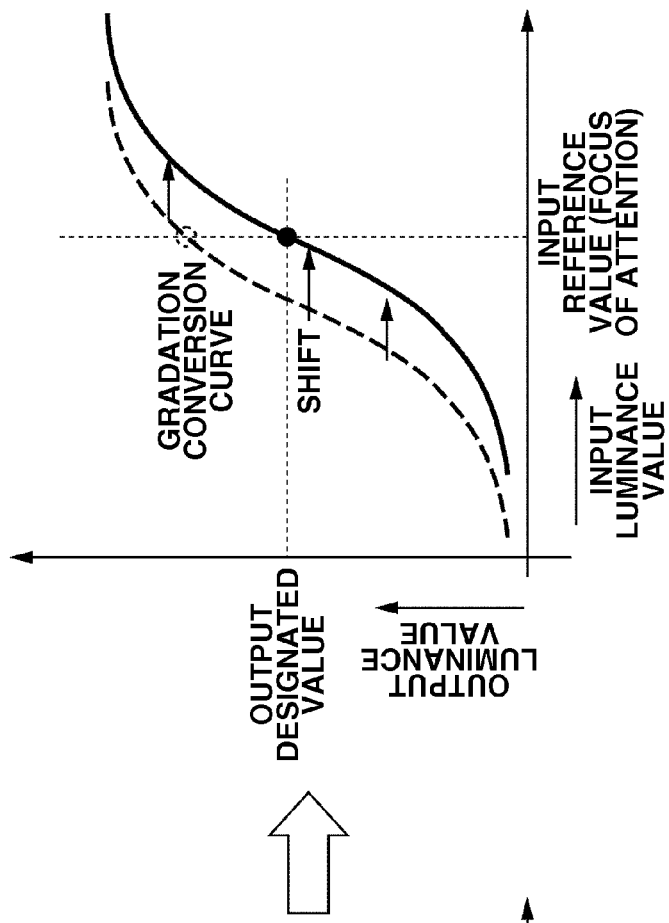

FIG. 7 is a schematic diagram illustrating an example of a configuration of the X-ray imaging system (radiation imaging system) according to the third exemplary embodiment of the present invention. In an X-ray imaging system 300 in illustrated FIG. 7, components similar to those in the first exemplary embodiment illustrated in FIG. 1 will be given the same reference numerals and their descriptions are not repeated.

Since the function of the communication unit in the X-ray sensor unit of the third exemplary embodiment is different from the communication unit illustrated in FIG. 1, it is denoted as a communication unit 327. Further, the X-ray sensor unit including the communication unit 327 is denoted as an X-ray sensor unit 320. Furthermore, according to the third exemplary embodiment, since the function of the X-ray control unit in the X-ray generation unit is different from the X-ray control unit illustrated in FIG. 1, it is denoted as an the X-ray control unit 311 and an X-ray generation unit including the X-ray control unit 311 is denoted as an X-ray generation unit 310.

According to the X-ray imaging system 300 illustrated in FIG. 7, similar to the X-ray imaging system 100 according to the first exemplary embodiment illustrated in FIG. 1, the X-ray sensor unit 320 and the main control unit 140 are connected via the external communication cable 130. Further, similar to the first exemplary embodiment, the X-ray sensor unit 320 corrects the sensor characteristics and transmits the obtained X-ray image data which has been subjected to the sensor characteristics correction to the main control unit 140 in the subsequent stage.

Further, similar to the first exemplary embodiment, the X-ray sensor unit 320 performs image analysis of the data of the X-ray image and calculates a pixel mean value of the X-ray image data as an analysis parameter. The pixel mean value of the X-ray image data is used as the analysis parameter in the description below, however, a minimum, a maximum, or a median value obtained from an analyzing result of the histogram of the X-ray image data, or a designated pixel value can be used as the analysis parameter. Further, a plurality of such values can be used as the analysis parameters.

The analysis parameter can be calculated using the radiation field region or the whole image. Further, it can be calculated using the region in the radiation field region other than the region in which the X-ray is directly applied to the two-dimensional X-ray sensor portion 121 without passing through the object H, or using a particular region. Information about the radiation field region can be acquired from the external apparatus as described in the first exemplary embodiment, or acquired by radiation field recognition processing of the X-ray image data performed in the X-ray sensor unit as described in the second exemplary embodiment.

The above described calculation processing of the pixel mean value is performed during performing the sensor characteristics correction processing or after the correction processing by inputting the pixel data in the image analysis unit (mean value calculation unit) 1242 when the pixel data is read from the frame memory in the storage unit 125.

According to the first exemplary embodiment, the analysis parameter calculated by the image analysis unit (mean value calculation unit) 1242 is used as a parameter for the gradation conversion processing performed by the image processing unit 1421 of the main control unit 140 in the subsequent stage. On the other hand, according to the present exemplary embodiment, the analysis parameter calculated by the image analysis unit (mean value calculation unit) 1242 in the X-ray sensor unit 320 is used as an X-ray control parameter for controlling the irradiation amount of the X-ray 113a applied to the object H from the X-ray generation unit 310 in real time.

The pixel mean value as the X-ray control parameter (radiation control parameter) can be transmitted from the communication unit 327 to the X-ray control unit 311 of the X-ray generation unit 310 at the same time that the X-ray image data is transmitted or prior to the transmission of the X-ray image data.

According to the X-ray control parameter received from the communication unit 327, the X-ray control unit 311 controls the irradiation amount of the X-ray 113a applied to the object H from the X-ray source 112 referring to an X-ray irradiation conversion table stored, for example, in the internal memory. Thus, the X-ray 113a of the irradiation amount determined by the X-ray control unit 311 is applied to the object H from the X-ray source 112.

Although it is desirable if the X-ray control parameter is transmitted to the X-ray generation unit 310 via a communication cable directly connected thereto, the parameter may also be transmitted to the X-ray control unit 311, for example, after it is once transmitted to the main control unit 140.

According to the present exemplary embodiment, the pixel mean value is calculated using the X-ray image data of one frame already stored in the X-ray sensor unit 320, and then the value is output to the X-ray generation unit 310 as the X-ray control parameter. Conventionally, the analysis performed on the main control unit side is started after the main control unit has received the X-ray image data for one frame, and then the X-ray control parameter has been obtained. However, according to the present exemplary embodiment, since the X-ray control parameter can be transmitted to the X-ray control unit 311 at earlier timing, the delay regarding the X-ray control can be reduced. Further, the delay of the reflection of the X-ray control parameter for a few frames does not occur.

Next, a fourth exemplary embodiment of the present invention will be described.

The configuration of the X-ray imaging system (radiation imaging system) according to the fourth exemplary embodiment is similar to that of the X-ray imaging system 300 according to the third exemplary embodiment illustrated in FIG. 7.

More specifically, the X-ray sensor unit 320 and the main control unit 140 are connected via the external communication cable 130. Further, the X-ray sensor unit 320 corrects the sensor characteristics and transmits the obtained X-ray image data which has been subjected to the sensor characteristics correction to the main control unit 140 in the subsequent stage.

Further, the X-ray sensor unit 320 performs image analysis of the data of the X-ray image and calculates a pixel mean value of the X-ray image data as an analysis parameter.

According to the above described first and second exemplary embodiments, the pixel mean value as the analysis parameter is transmitted to the main control unit 140 as the gradation conversion parameter. According to the third exemplary embodiment, the pixel mean value is transmitted to the X-ray generation unit 310 as the X-ray control parameter.

On the contrary, according to the present exemplary embodiment, the pixel mean value as the analysis parameter is transmitted to the main control unit 140 as the gradation conversion parameter and also transmitted to the X-ray generation unit 310 as the X-ray control parameter. In this case, similar to the first exemplary embodiment, the gradation conversion parameter is embedded in the header portion of the X-ray image data when the data is transmitted to the main control unit 140.

Further, the image processing unit 1421 of the main control unit 140 immediately starts the image processing upon receiving the X-ray image data whose amount is more than or equal to the minimum amount of data necessary for the image processing using the gradation conversion parameter.

Further, although the pixel mean value is used as the gradation conversion parameter as well as the X-ray control parameter in the description above, it is not always necessary to use the same pixel mean value as the parameters. For example, a median value of a result of a histogram analysis can be used as the gradation conversion parameter and the pixel mean value can be used as the X-ray control parameter.

According to the present exemplary embodiment, since the gradation conversion parameter can be transmitted to the main control unit 140 together with or prior to the transmission of the X-ray image data, the main control unit 140 can immediately start the image processing using the gradation conversion parameter upon receiving the image data. In this manner, the delay in the display of the image can be prevented. Further, the delay in the reflection of the gradation conversion parameter for a few frames does not occur. Since the X-ray control parameter can be transmitted to the X-ray generation unit 310 in advance, the delay in the control of the X-ray can be reduced. Additionally, the delay of the reflection of the X-ray control parameter for a few frames does not occur.

Aspects of the present invention can also be realized by a computer of a system or apparatus (or devices such as a CPU or MPU) that reads out and executes a program recorded on a memory device to perform the functions of the above described embodiment(s), and by a method, the steps of which are performed by a computer of a system or apparatus by, for example, reading out and executing a program recorded on a memory device to perform the functions of the above described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-179628 filed Jul. 31, 2009, which is hereby incorporated by reference herein in its entirety.

What is claimed is:

1. A radiation imaging system that includes a radiation sensor unit configured to generate radiation image data based on a radiation ray that passes through an object and a main control unit configured to receive the radiation image data,
   the radiation sensor unit comprising:
      a radiation sensor configured to detect the radiation ray that passes through the object as a radiation image signal;
      an analog to digital converter configured to convert the radiation image signal into a digital signal as the radiation image data;
      a sensor characteristics correction unit configured to perform sensor characteristics correction on the radiation image data based on image reception characteristics of the radiation sensor;
      an image analysis unit configured to calculate, based on the radiation image data in which the sensor characteristics correction is performed, an analysis parameter; and
      a transmission unit configured to transmit the analysis parameter as a gradation conversion parameter and the radiation image data which has been subjected to the sensor characteristics correction to the main control unit; and
   the main control unit comprising:
      a reception unit configured to receive the gradation conversion parameter and the radiation image data which has been subjected to the sensor characteristics correction;
      a gradation conversion processing unit configured to perform gradation conversion processing on the radiation image data which has been subjected to the sensor characteristics correction based on the gradation conversion parameter,
   wherein, when the transmission unit transmits the gradation conversion parameter together with the radiation image data which has been subjected to the sensor characteristics correction, the transmission unit embeds the gradation conversion parameter in a header portion of the radiation image data which has been subjected to the sensor characteristics correction in transmitting the gradation conversion parameter,
   the main control unit further includes a reception determination unit configured to determine whether the radiation image data transmitted by the transmission unit more than or equal to a minimum processing amount of data necessary to perform the gradation conversion processing based on the gradation conversion parameter received at the main control unit, and
   when the reception determination unit determines that the radiation image data more than or equal to the minimum processing amount is received, the gradation conversion processing unit immediately starts the gradation conversion processing.

2. The radiation imaging system according to claim 1, wherein the gradation conversion parameter is at least one of a pixel mean value relating to the radiation image data, and a maximum value, a minimum value, and a median value of a histogram analysis of the radiation image data.

3. The radiation imaging system according to claim 1, wherein when the radiation image data which has been subjected to the sensor characteristics correction is transmitted, the transmission unit divides the radiation image data which has been subjected to the sensor characteristics correction into units of communication packets or into predetermined units, and transmits each piece of the divided image to the main control unit.

4. The radiation imaging system according to claim 1, wherein when the analysis parameter is calculated, the image analysis unit calculates the analysis parameter only from a pixel in a radiation field region of the radiation image data which has been subjected to the sensor characteristics correction based on radiation field region information acquired from an external apparatus or by radiation field recognition with respect to the radiation image data which has been subjected to the sensor characteristics correction.

5. The radiation imaging system according to claim 1, wherein the main control unit further includes a control unit configured to perform control at least to display or to store the radiation image data processed by the gradation conversion processing unit.

6. The radiation imaging system according to claim 1, wherein the radiation sensor unit further includes a storage unit configured to store the radiation image data detected by the radiation sensor, and
   wherein the sensor characteristics correction unit performs the correction processing of the sensor characteristics with respect to the radiation image data stored in the storage unit.

7. The radiation imaging apparatus system of claim 1, wherein the transmission unit transmits the analysis parameter together with the radiation image data which has been subjected to the sensor characteristics correction.

8. The radiation imaging apparatus system of claim 1, wherein the transmission unit transmits the analysis parameter prior to the transmission of the radiation image data which has been subjected to the sensor characteristics correction.

9. A method for controlling a radiation imaging system that includes a radiation sensor unit configured to generate radiation image data based on a radiation ray that passes through an object and a main control unit configured to receive the radiation image data, the method comprising:
  detecting a radiation image signal, using the radiation sensor unit, based on the radiation ray that passes through the object;
  converting the radiation image signal into a digital signal data as radiation image data;
  performing sensor characteristics correction on the radiation image data based on image reception characteristics of the radiation sensor unit;
  calculating an analysis parameter, based on the radiation image data in which the sensor characteristics correction is performed;
  embedding the analysis parameter as a gradation conversion parameter in a header portion of the radiation image data which has been subjected to the sensor characteristics correction;
  transmitting with a transmission unit the radiation image data including the gradation conversion parameter;
  receiving the radiation image data at the main control unit;
  determining whether the radiation image data transmitted by the transmission unit more than or equal to a minimum processing amount of data necessary to perform gradation conversion processing based on the gradation conversion parameter is received at the main control unit; and
  starting, at the main control unit, gradation conversion processing of the radiation image data which has been subjected to the sensor characteristics correction based on the gradation conversion parameter, immediately after a determination in the determining that the radiation image data more than or equal to the minimum processing amount is received.

10. A non-transitory computer-readable medium storing thereon a computer-executable program for causing a computer to execute a method according to claim 9.

11. A control apparatus for radiation imaging with a radiation sensor, comprising:
  a reception unit configured to receive a gradation conversion parameter and radiation image data which has been subjected to sensor characteristics correction;
  a gradation conversion processing unit configured to perform gradation conversion processing on the radiation image data which has been subjected to the sensor characteristics correction based on the gradation conversion parameter; and
  a reception determination unit configured to determine whether the radiation image data transmitted by a transmission unit more than or equal to a minimum processing amount of data necessary to perform the gradation conversion processing based on the gradation conversion parameter received at the reception unit,
  wherein the gradation conversion processing unit is configured to start the gradation conversion processing in response to a determination of the reception determination unit that a part of the radiation image data more than or equal to the minimum processing amount is received.

12. A control method for imaging with a radiation sensor configured to generate radiation image data based on a radiation ray that passes through an object, the method comprising:
  receiving, at a main control unit, a gradation conversion parameter and radiation image data which has been generated by the radiation sensor and has been subjected to sensor characteristics correction;
  determining, at the main control unit, in parallel with the receiving, whether an amount of the received radiation image data exceeds or equals to a minimum amount of data necessary to perform gradation conversion processing; and
  starting the gradation conversion processing, at the main control unit, based on the gradation conversion parameter on the radiation image data which has been subjected to the sensor characteristics correction, in response to a determination in the determining that the amount of the received radiation image data exceeds or equals to the minimum amount.

* * * * *